United States Patent [19]
Sato

[11] 3,982,529
[45] Sept. 28, 1976

[54] BIOELECTRODES

[76] Inventor: Takuya R. Sato, 5130 Randall St., Culver City, Calif. 90230

[22] Filed: Aug. 7, 1975

[21] Appl. No.: 602,611

Related U.S. Application Data

[63] Continuation-in-part of Ser. No. 483,181, June 25, 1974, abandoned, and a continuation-in-part of Ser. No. 492,367, July 29, 1974, abandoned, which is a continuation-in-part of Ser. No. 228,827, Feb. 24, 1972, Pat. No. 3,834,373.

[52] U.S. Cl. .............................. 2.06 E; 128/2.1 E; 128/417; 128/DIG. 4
[51] Int. Cl.² ............................................ A61B 5/04
[58] Field of Search ........... 128/2.06 E, 2.1 E, 404, 128/417, 418, DIG. 4

[56] References Cited
UNITED STATES PATENTS

| | | | |
|---|---|---|---|
| 3,157,181 | 11/1964 | McCarty | 128/2.1 E |
| 3,187,745 | 6/1965 | Baum et al. | 128/2.06 E |
| 3,545,432 | 12/1970 | Berman | 128/2.06 E |
| 3,574,305 | 4/1971 | Muhl | 128/2.1 E |
| 3,590,822 | 7/1971 | Ackerman | 128/404 |
| 3,606,881 | 9/1971 | Woodson | 128/2.06 E |
| 3,610,229 | 10/1971 | Zenkich | 128/2.06 E |
| 3,669,110 | 6/1972 | Low et al. | 128/2.1 E |
| 3,701,346 | 10/1972 | Patrick, Jr. et al. | 128/2.06 E |
| 3,720,209 | 3/1973 | Bolduc | 128/2.06 E |
| 3,788,317 | 1/1974 | McCormick | 128/2.06 E |
| 3,805,769 | 4/1974 | Sessions | 128/2.06 E |
| 3,830,229 | 8/1974 | Johnson | 128/2.06 E |
| 3,868,946 | 3/1975 | Hurley | 128/2.1 E |

*Primary Examiner*—Robert W. Michell
*Assistant Examiner*—Lee S. Cohen
*Attorney, Agent, or Firm*—Benoit Law Corporation

[57] ABSTRACT

Bioelectrodes applicable to body parts comprise an electrically insulating structure having a bottom portion and a lateral wall portion defining a cavity. An electrode is located at the bottom portion. A pad of electrolyte-absorbent resilient material is located in the cavity and is dimensioned to leave a lateral space between the pad and the wall portion and is further dimensioned to contact the electrode at the bottom portion and to project out of the cavity in a relaxed condition. A removable cover on the electrically insulating structure is constructed to compress the resilient pad completely into the cavity.

Other bioelectrodes applicable to body parts comprise a silver, silver chloride electrode having an electrically insulating, water impermeable, inert organic matrix, a pad for retaining an electrolyte at this electrode, and a container for the electrode and the electrolyte pad. An adhesive between the electrolyte pad and the container is independent of the electrode matrix and anchors the electrolyte pad in the container.

41 Claims, 5 Drawing Figures

U.S. Patent   Sept. 28, 1976   3,982,529
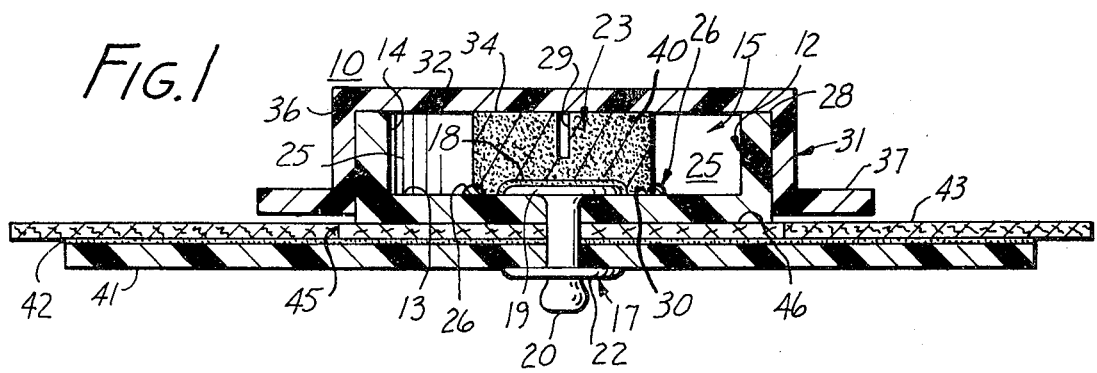
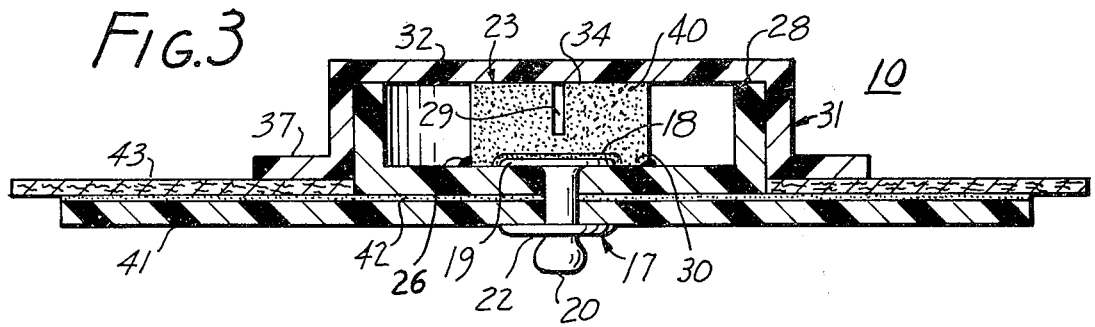
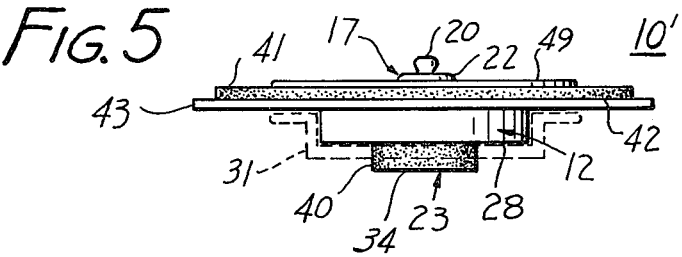
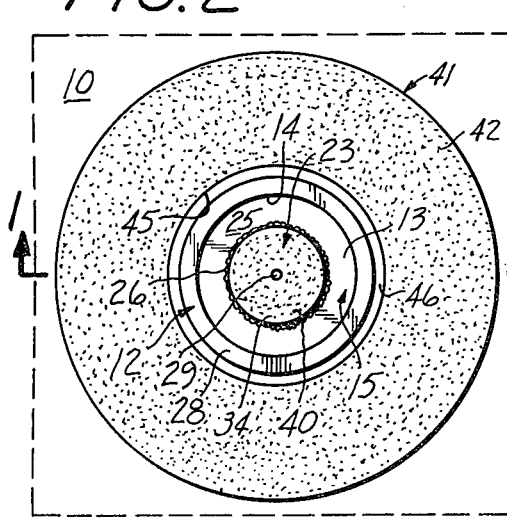
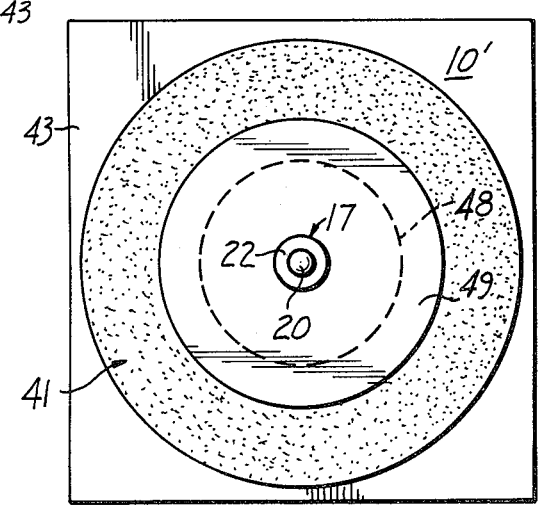

BIOELECTRODES

CROSS-REFERENCE

This is a continuation-in-part of United States Patent Application Ser. No. 483,181, now abandoned entitled Bioelectrodes, filed June 25, 1974, by the subject inventor, and herewith incorporated by reference herein, and a continuation-in-part of United States Patent Application Ser. No. 492,367, now abandoned entitled Bioelectrodes, filed July 29, 1974, by the subject inventor, which in turn is a continuation-in-part of United States Application Ser. No. 228,827, now U.S. Pat. No. 3,834,373, entitled Silver, Silver Chloride Electrodes, filed Feb. 24, 1972, and herewith incorporated by reference herein.

BACKGROUND OF THE INVENTION

1. Field of the Invention

The subject invention relates to bioelectrodes applicable to body parts of living subjects to detect electrical signals and for similar purposes.

2. Description of the Prior Art

Bioelectrodes have sometimes been designed so as to permit direct physical contact of an electrode or a metallic part acting as an electrode with the skin of the subject to which the electrode is applied. Such direct physical contact has prevented proper operation of the electrode in its requisite electrolytic environment and has, moreover, introduced artifactitious signals or motion generated noise into the detected electrical body signals, thereby rendering the bioelectrode inoperative for its intended purpose.

In order to overcome this disadvantage, the prior art evolved electrode designs in which the metallic electrode was maintained spaced from the skin of the subject and in which a liquid or jellylike electrolyte is disposed between the electrode and the subject's skin. In practice, that design did not generally perform well because of the fluid nature of the electrolyte which did not assure a constant and reliable electrolytic contact between the electrode and the subject's skin.

To overcome these disadvantages, it has been proposed to cover the electrode with an electrolyte-absorbent pad, such as a piece of sponge or felt, for reliably retaining the requisite electrolyte between the electrode and the subject's skin. In order to provide for an intimate contact of the electrolyte pad with the subject's skin and in an effort to reduce the loss of electrolyte from the pad during the use of the electrode, a circular skirt of rubber or another material having a flexibility similar to that of the skin has frequently been arranged around the electrolyte pad. In practice, this encumbered the assembly of the electrode structure and introduced problems of wear and tear. Moreover, this "suction cup" approach did not consistently assure the requisite uniform application of the electrode pad to the subject's skin.

Accordingly, a type of design evolved in which the bioelectrode included a cup of electrically insulating material or an equivalent structure that defined a cavity at the bottom of which the metallic electrode was located. That cavity was provided with an electrolyte pad which essentially completely filled the cavity and tended to project to the outside thereof for an intimate contact with the subject's skin.

The feature of the electrolyte pad essentially completely filling the electrode structure cavity was thought important for several reasons.

For instance, some researchers strove for a maximum cross-section of the electrolytic current conducting paths by filling the entire cross-section of the electrode structure cavity with electrolyte retaining material.

Other prior-art workers essentially completely filled the electrode cavity with an electrolyte retaining pad in order to preclude the existence of any substantial clearance between the electrolyte pad and the inner walls of the cavity. There were several reasons for this prior-art methodology. In some instances, an intimate abutment of the electrolyte pad against the lateral inside walls as well as against the bottom of the cavity was thought important for the achievement of an intimate pressure of the electrolyte pad against the subject's skin. In other instances, the existence of free space between the electrolyte pad and the cavity walls was thought to foster an accumulation of extruded electrolyte which could have interfered with the sealing of the electrode structure in cases where a protective stripable cover was applied to the electrode pad and was retained on the electrode cavity by an adhesive.

Another reason for essentially completely filling the cavity with the electrolyte pad was added to the above mentioned list when open-cell foamed pads of urethane or another material which is not of itself electrolyte-absorbent came into use as electrolyte retaining vehicles in bioelectrodes.

Typically, such open-cell pads are filled with electrolyte during the manufacture of the bioelectrodes. Equally typically, these types of electrolyte pads are provided with a thickness greater than the depth of the electrode structure cavity whereby the pad tends to project outwardly of the cavity into intimate contact with the subject's skin. To appreciate the difficulty prevailing with that type of prior-art bioelectrode, it is necessary to visualize that in the case of an open-cell pad of a material that is hydrophobic and thus not of itself capable of retaining any electrolyte, all the electrolyte stored in the pad is of necessity contained inside the open cells thereof. Accordingly, electrolyte is inevitably extruded from the pad when the cells thereof are diminished in size. The latter is the case when the electrolyte pad is compressed into the cavity.

No serious consequences would ordinarily flow from such an extrusion of electrolyte if the pad compression took place when the bioelectrode is applied to the subject's skin. However, if the protruding electrolyte pad is depressed during the manufacture of the bioelectrode, such as during the application of a removable cover to the cavity, and is then relaxed prior to the application of the bioelectrode to the subject's skin, such as at the occasion of a removal of the latter cover, serious consequences can result from the existence of a free space between the electrode pad and the wall of the electrode cavity filled with air.

The reason for this resides in the fact that electrolyte is extruded into that free space when the electrolyte pad is first compressed, such as during the application of a protective cover as indicated above. When thereafter the electrode pad is relaxed, such as during the removal of the protective cover prior to an application of the electrode to the skin, there is no guarantee that the extruded electrolyte will be completely sucked back into the pad. Rather, most of the extruded electrolyte will not be able to reenter the cells inside the pad in a typical situation but will be replaced by air. Accordingly, since the pad in the prior-art version under consideration is not of an electrolyte-absorbent material, the electrolyte paths inside the pad will be interrupted by the entrapped air when the pad is decompressed or relaxed prior to application of the bioelectrode to the subject's skin.

Due to the persistence of these difficulties, the prior art eventually evolved a design in which the traditional feature of the electrolyte pad essentially completely filling the electrode cavity was retained and in which a removable protective cover had a raised portion overlying the pad and having a height greater than the height of the cavity so that the applied protective cover would accommodate the greater thickness of the pad above the electrode cavity. This, however, generated some further problems so that it eventually became necessary in practical bioelectrode devices to provide the raised portion of the protective cover with a projection which engaged the electrolyte pad for holding that pad inside the electrode cavity.

This, in turn tended to deplete a central region of the pad of electrolyte and to impose a permenant deformation on the pad during prolonged storage, thereby placing into jeopardy the desired uniform contact of the electrolyte with the subject's skin. Moreover, the increased height of the assembled bioelectrode necessitated by the above mentioned raised cover portion worked against the modern trend toward low-profile bioelectrodes and toward increased savings of materials which are periodically in short supply.

In a similar vein a type of prior-art electrode provided an electrode plate with lateral hooks which were driven into the side of the electrolyte sponge. This was highly undesirable from an electrochemical point of view, since these hooks encouraged formation of motion sensitive, artifactitious current conducting paths along the side of the electrolyte pad and in detrimental shunt relationship to the path through and inside the pad between the main proper of the electrode and the adjacent body part. Also, these hooks impaired the structural integrity of the electrolyte pad and required special equipment and steps for their application to the pad.

Due to the persistence of these difficulties, the prior art eventually evolved designs in which the electrolyte pad was simply placed into the electrode cavity and was retained therein by a removable protective cover.

This, of course, engendered the danger that the electrolyte pad would fall out of the cavity when the cover was removed prior to application of the electrode to a body part. The prior art, therefore, provided the removable cover with a projection which engaged the electrolyte pad for holding that pad inside the electrode cavity. However, that proposal could not operate satisfactorily, since that projecting portion depleted a central region of the pad of electrolyte and imposed a permanent deformation on the pad during prolonged storage, thereby placing into jeopardy the desired uniform contact of the electrolyte with the subject's skin. Moreover, the electrolyte pad still tended to fall out of the electrode cavity when the cover with the mentioned projection was removed from the electrode proper.

SUMMARY OF THE INVENTION

It is a broad object of the invention to overcome the above mentioned disadvantages.

It is a related object of the invention to provide improved bioelectrodes.

Other objects of the invention will become apparent in the further course of this disclosure.

From one aspect thereof, the invention resides in a bioelectrode applicable to a body part, comprising in combination an electrically insulating structure having a bottom portion and a lateral wall portion defining a cavity, electric current conducting means including an electrode at said bottom portion, means for retaining electrolyte, including a pad of electrolyte-absorbent resilient material in said cavity contacting said electrode at said bottom portion and projecting out of said cavity in an electrolyte containing relaxed condition, a lateral space between said pad and said wall portion, a removable cover on said structure compressing said resilient pad completely into said cavity, said lateral space being of a size to completely accommodate said pad when compressed completely into said cavity by said cover, and means for attaching said structure to a body part.

As will be more fully shown in the further course of this disclosure, employment of an electrolyte-absorbent resilient material for the electrolyte retaining pad and the dimensioning of the pad to provide for the existence of a lateral space between the pad and the wall portion has the significant advantage of immunizing the bioelectrode to the previously observed adverse effects of a compression and subsequent relaxation of the electrolyte pad. Accordingly, the subject invention combines these features concerning the electrolyte pad with a construction of the mentioned removable cover which compresses the resilient pad completely into the cavity, thereby minimizing the height and bulk of the assembled electrode and realizing a saving of presently critical materials.

In accordance with a preferred embodiment of the subject invention, the wall portion of the electrically insulating electrode structure is rigid, so as to more reliably prevent movement of the applied electrode relative to the adjacent body part and flow of electrolyte beyond the confines of the bioelectrode proper.

In accordance with a further preferred embodiment, the bioelectrode according to the subject invention includes means for anchoring the electrolyte pad in the cavity. This considerably improves freedom of electrode design and handling by preventing the electrolyte pad, dimensioned as herein defined, from falling out of the electrode cavity or from otherwise dislodging itself relative to the metallic electrode at the bottom of the insulating electrode structure.

The utility of the bioelectrode according to the subject invention, extends from fields involving the measurements of electrical body signals to other areas, such as those concerned with the application of electric currents or the iontophoretic application of substances to body parts.

From another aspect thereof, the invention resides in a bioelectrode comprising in combination a silver, silver chloride electrode comprising a plurality of silver particles, a plurality of silver chloride particles, and an electrically insulating, water impermeable, inert organic matrix for said silver particles and said silver chloride particles, said silver particles and said silver chloride particles being interspersed with each other in and throughout said matrix, and said interspersed silver particles and silver chloride particles being in electrical contact with each other, an electrical conductor connected to said silver, silver chloride electrode, means for retaining an electrolyte at said silver, silver chloride electrode, container means for said silver, silver chloride electrode and for at least part of said conductor and said electrolyte-retaining means, an adhesive between said electrolyte retaining means and said container means, said adhesive being independent of said matrix and anchoring said electrolyte retaining means in said container means, and silver particles being present in said organic matrix in an amount of from 15 to 70% by volume of said organic matrix with said interspersed silver particles and silver chloride particles, said silver chloride particles being present in said organic matrix in an amount of from 0.2 to 15% by colume of said organic matrix with said interspersed silver particles and silver chloride particles, and said organic matrix constituting essentially the balance of the volume of said organic matrix with said interspersed silver particles and silver chloride particles.

From a further aspect thereof, the invention resides in a bioelectrode comprising in combination a silver, silver chloride electrode comprising a plurality of silver particles, a plurality of silver chloride particles, and an electrically insulating, water impermeable, inert organic matrix for said silver particles and said silver chloride particles, said silver particles and said silver chloride particles being interspersed with each other in and throughout said matrix, and said interspersed silver particles and silver chloride particles being in electrical contact with each other, an electrical conductor connected to said silver, silver chloride electrode, means for retaining an electrolyte at said silver, silver chloride electrode, container means for said silver, silver chloride electrode and for at least part ot said conductor and said electrolyte-retaining means, an adhesive between said electrolyte retaining means and said container means, said adhesive being independent of said matrix and anchoring said electrolyte retaining means in said container means, said silver particles being present in said organic matrix in an amount of from 70 to 90% by weight of said organic matrix with said interspersed silver particles and silver chloride particles, said silver chloride particles being present in said organic matrix in an amount of from 0.5 to 15% by weight of said organic matrix with said interspersed silver particles and silver chloride particles, and said organic matrix constituting essentially the balance of the weight of said organic matrix with said interspersed silver particles and silver chloride particles.

BRIEF DESCRIPTION OF THE DRAWINGS

The subject invention and its objects will become more readily apparent from the following detailed description of preferred embodiments thereof, illustrated by way of example in the accompanying drawings in which like reference numerals designate like or functionally equivalent parts and in which:

FIG. 1 is a section through a bioelectrode according to a preferred embodiment of the subject invention, taken along the line 1 — 1 in FIG. 2;

FIG. 2 is a top view of the bioelectrode of FIG. 1, with certain parts having been removed for better visibility of the electrode structure;

FIG. 3 is a view similar to FIG. 1 showing a bioelectrode in accordance with a further embodiment of the subject invention;

FIG. 4 is a bottom view of a bioelectrode in accordance with yet another preferred embodiment of the subject invention; and FIG. 5 is a side view of the bioelectrode shown in FIG. 4.

The FIGS. 1 and 3 are drawn to a larger scale than the FIGS. 2, 4 and 5.

DESCRIPTION OF PREFERRED EMBODIMENTS

The bioelectrode 10 according to the preferred embodiment shown in FIGS. 1 and 2 has an electrically insulating structure or cup 12 having a bottom portion 13 and a lateral wall portion 14 defining a cavity 15. By way of example, and not by way of limitation, the cup 12 may be molded or otherwise formed of a plastic, such as polyethylene, polypropylene, vinyl, a polyallamer copolymer, and a styrenebutadiene copolymer.

Electric current conducting equipment 17 includes an electrode 18 at the bottom 13 of the cavity 15. Suitable electrode materials are well known in the bioelectrode art. By way of example, the electrode 18 may be a silver, silver chloride electrode of the type frequently employed in bioelectrodes. By way of further example, the electrode 18 may be a silver, silver chloride electrode of the type disclosed in my U.S. Pat. No. 3,834,373, issued Sept. 10, 1974, which is herewith incorporated by reference herein. That type of electrode comprises a plurality of silver particles, a plurality of silver chloride particles, and an electrically insulating, water impermeable inert organic matrix for the silver particles and silver chloride particles. These silver particles and silver chloride particles are preferably interspersed with each other in and throughout the matrix, and these interspersed silver particles and silver chloride particles are in electrical contact with each other.

The metallic electrode 18 is applied to or deposited on the inner part 19 of a snap fastener 20. Such inner part 19 extends through an aperture in the bottom portion 13 of the electrode cup 12 and is pressed into an outer fastener part 22 to form a swaged unit. In practice, the male snap fastener 20 cooperates with a corresponding female complement in order to connect the bioelectrode to suitable electronic equipment such as an electrocardiograph (ECG) or other bioelectric instruments as disclosed in my U.S. Pat. No. 3,834,373, issued Sept. 10, 1974 and herewith incorporated by reference herein.

Means for retaining electrolyte in the bioelectrode comprise a pad 23 located in the cavity 15 in the cup 12. According to an essential feature of the subject invention, the pad 23 is of electrolyte-absorbent resilient material. In other words, the pad 23 is of hydrophilic material, which distinguishes the subject invention from those prior-art bioelectrodes which employ a pad of foamed urethane or other hydrophobic material, whereby the electrolyte was retained in the open cells of the foamed pad structure rather than in the material of the pad itself.

Several natural or man-made structures are suitable for the electrolyte pad employed in the practice of the subject invention, as long as they possess fibers, membranes or wall portions capable of hydrophilically taking up the aqueous or liquid electrolyte employed in the bioelectrode 10.

By way of example, suitable materials for the electrolyte pad 23 include carbohydrates, such as the polysaccharides, having the desired electrolyte-absorbent quality. For instance, a pad structure formed of cellulose fibers may be employed at 23.

Suitable specific examples include felt, blotting paper and a sponge of a type having structure, such as fibers, capable of absorbing the aqueous or liquid electrolyte.

In my experiments, I have come to prefer electrolyte pads 23 made of a natural sponge, such as the skeleton of a sea animal known under the general classification of phylum porifera, or a cellulose sponge composed of fibers capable of absorbing the aqueous or the liquid electrolyte. Since pads of this type retain the electrolyte in the wall or fiber structure, rather than only inside of open or closed cells, it is practically impossible to dehydrate the pad 23 of electrolyte by mere compression during the practical use of the bioelectrode and the presence of air bubbles is of no consequence.

The electrolyte pad 23 of the bioelectrode according to the subject invention can thus endure alternate compression and relaxation without an interruption of the electrolyte paths between the metallic electrode 18 and the skin of the subject to which the bioelectrode is applied during use thereof.

According to a further feature of the subject invention, the electrolyte pad 23 is dimensioned to leave a lateral space 25 between the pad 23 and the inside surface of the wall 14 of the cup 12.

In the illustrated preferred embodiment, and by way of example, the wall portion 14 is hollow-cylindrical and the pad 23 is spaced from any part of this hollow-cylindrical wall portion. In fact, the pad 23 is preferably though not necessarily, of a cylindrical configuration, and is dimensioned to leave an annular space between the pad 23 and the wall portion 14.

In accordance with a preferred embodiment of the subject invention, the bioelectrode 10 includes means for anchoring the pad 23 in the electrode cavity 15. By way of example, a preferably electrically insulating adhesive 26 may be employed for attaching or anchoring the electrolyte pad 23 to the bottom portion 13 of the electrode cup 12. Alternatively or additionally, the organic matrix of the electrode 18 may itself be employed to attach the electrolyte pad to the electrode when a silver, silver chloride electrode of the type disclosed in the above mentioned parent application or patent is employed. In other words, the anchoring means for the pad 23 may be included in the electrode 18 at the bottom portion.

The height of the pad 23 may be considerably smaller than the height of the cavity 15 when the pad is in its dry condition. For instance, a sponge of cellulose fiber may increase in thickness by more than three times from its dry state when it is being saturated with electrolyte. Irrespective of what hydrophilic material is employed for the pad 23 in the practice of the subject invention, it is essential that the pad 23 be also dimensioned to contact the electrode 18 at the bottom portion 13 and to project out of the cavity 15 in an electrolyte containing relaxed condition. In this manner, a reliable contact of the pad 23 with the subject's skin is assured during use of the electrode. An example of an electrolyte pad 23 projecting out of the cavity 15 beyond the level of the top rim portion 28 of the electrode cup 12 is seen in FIG. 5.

In the preparation of the bioelectrode 10, the electrolyte is applied to the pad 23 until it thoroughly permeates the same. In accordance with a preferred embodiment of the subject invention, the pad 23 has a central aperture 29 capable of receiving a hypodermic needle or other conduit through which the pad may be saturated with electrolyte from a syringe or other pressurized electrolyte supply. Use of this aperture 29 with devices of the latter type has proved to be very effective in rapidly, thoroughly and reliably providing the pad with the requisite electrolyte.

The bioelectrode assembly 10 includes a removable cover 31 constructed to compress the resilient pad 23 completely into the cavity 15 of the electrode cup 12. The removable cover 31 is preferably of an electrically insulating material, such as a molded or otherwise formed plastic. By way of example, and not by way of limitation, suitable materials for the cover 31 include the same materials as employed for the cup 12. If desired, the cup 12 and the cover 31 may be made of different materials if differences in shrinking factors and other characteristics are properly taken into consideration.

The removable cover 31 in the illustrated preferred embodiments has a flat lid portion which, at its lower surface facing the cavity 15, physically contacts all of the adjacent top surface 34 of the electrolyte pad 23.

In this manner, the electrolytically active surface of the pad 23, which contacts the subject's skin when the electrode is in use, is protected against prolonged exposure to air, and an evaporation or other detrimental loss of electrolyte is conveniently inhibited.

It will also be noted that the lid portion 32 of the removable cover 31 in the illustrated preferred embodiment also contacts the rim 28 of the electrode cup 12 opposite its bottom portion 13. In this manner, the relatively low profile of the electrode cup 12 is not substantially augmented by the applied removable cover 31. At the same time, the rim portion 28 of the electrolyte cup 12 provides stops for preventing the cover 31 from being pushed downwardly to an extent which would excessively squeeze the pad 34 during prolonged storage of the bioelectrode.

It will be noted that the construction according to the illustrated preferred embodiments of the invention compares itself very advantageously to those prior-art designs in which the lid portion of the removable cover was substantially raised relative to the rim portion of the electrolyte cup and in which a conical projection jutted into the electrolyte pad and toward the metallic electrode at the bottom of the electrolyte cavity.

As disclosed above, and as more fully shown in FIG. 5, the electrolyte pad 23 is dimensioned to project out of the cavity 15 beyond the level of the rim portion 28 of the electrode cup when the removable cover 31 is not located on the electrode cup and when the pad 23 has been supplied with the electrolyte. The cover 31 may then be applied to the electrolyte cup by sliding an annular wall portion 36 of the cover along the outside of the wall portion 14 of the electrolyte cup 12. The cover wall portion 36 is dimensioned relative to the cup wall portion 14 so as to slide relatively easily therealong. The cover 31 has an annular rim or flange portion 37 for facilitating the manual removal of the cover 31 from the cup 12. If desired, humps, bead portions or fit points (not shown) may be provided on either or both of the outer surface of the cup wall portion 14 and the inner surface of the cover wall portion 36 to provide for a releasable retention of the cap 31 on the cup 12.

Complete compression of the electrolyte pad 23 into the cavity 25 by the cover lid portion 32 has no detrimental effect on the bioelectrodes. In particular, the existence of the annular space 25 between the pad 23 and the electrode cup wall portion 14 provides the electrode pad 23 with a certain freedom of lateral movement, whereby the electrolyte pad is capable of expanding or bulging laterally or radially to some extent without material extrusion of electrolyte from the pad 23. This stands in favorable contrast to those prior-art designs in which an electrolyte pad which completely filled the electrode cavity would inevitably and immediately start to exude electrolyte when compressed into the cavity.

Moreover, electrolyte extruded upon a further compression of the pad 23 can readily flow into the annular space about the pad 23. Due to the electrolyte-absorbent nature of the material from which the pad 23 is formed, no excessive depletion of electrolyte from the pad 23 can occur during compression of the pad, and no interruption of the electrolytic paths between the metallic electrode 18 and the top surface 34 of the pad can occur during relaxation of the pad following its previous compression.

Accordingly, the performance of the bioelectrode 10 is characterized by high quality, accuracy and reliability. In order to inhibit loss of electrolyte along the subject's skin and in order to avoid artifactitious currents or motion sensitivity of the bioelectrode, we presently prefer to make the wall portion 14 if not the entire electrode cup of a rigid material, such as one of the molded plastics mentioned above.

The bioelectrode with the projecting electrolyte pad 34 may be applied to the subject's skin or body part in a variety of ways. By way of example, the illustrated bioelectrode assembly 10 includes a circular elastic sheet 41 which has an adhesive 42 on a surface thereof for convenient application of the bioelectrode to the user's skin or body parts. A peelable glazed or waxed protective strip 43 is located on the adhesive 42 and is, of course, removed to expose the adhesive prior to application of the bioelectrode.

The protective strip 43 may be circular like the sheet 41 or may be rectangular as indicated in FIGS. 2, 4 and 5.

As illustrated in FIG. 1, a central portion 46 of the strip 43 may be located between the elastic sheet 41 and the electrode cup 12. In that case, the strip 43 has a circular cut 45 to permit easy removal of the peripheral portion of the strip 43 from the adhesive 42.

A somewhat different construction is shown in FIG. 3, where the peelable protective strip 43 is annular and stops short of the electrode cup 12. In practice, it will be found that the embodiment according to FIG. 1 is easier to manufacture with conventional machinery than the embodiment of FIG. 3. In either case, the snap fastener part 22 cooperates with the snap fastener part 19 in retaining the elastic sheet 41 assembled with the electrode cup 12.

The preferred embodiments of the subject invention illustrated in FIGS. 1 and 3 are sufficiently rugged for the majority of applications. However, the construction according to the further preferred embodiment illustrated in FIGS. 4 and 5 may be employed if desired.

The difference between the preferred embodiment shown in FIGS. 4 and 5 and the preferred embodiments shown in FIGS. 1 to 3 is that the elastic sheet 41 does not extend to the snap fastener structure 17. Rather, the adhesive elastic sheet 41 in the embodiment of FIGS. 4 and 5 is annular, having an inner circular edge 48 which surrounds the electrode cup 12.

According to FIGS. 4 and 5, a circular sheet 49 of flexible but essentially non-stretchable material connects the elastic sheet 41, which preferably is stretchable, to the electrode cup 12 with the aid of the snap fastener structure 17. To this end, the sheet 49 has a peripheral portion overlapping the sheet 41 and being attached thereto in any desired manner, such as by means of a conventional adhesive. Suitable materials for the flexible but essentially non-stretchable central sheet 49 include vinyl, polyethylene, polyester, polypropylene, and paper, for example.

The remainder of the bioelectrode 10' according to the preferred embodiment of FIGS. 4 and 5 may be the same as the bioelectrode 10 according to the other preferred embodiments.

As shown in FIGS. 1 and 3, the electrolyte pad 23 has a first end portion 30 adjacent the electrode 18 or bottom portion 13, and a second end portion 40 adjacent the cavity opening surrounded by the top rim portion 28 of the electrode cup.

In accordance with the preferred embodiment of the subject invention illustrated in FIGS. 1 and 2, the bioelectrode 10 includes an adhesive 26 attached to the first end portion 30 of the pad 23 for anchoring the pad 23 in the cavity 15. By way of example, the adhesive 26 may be attached to the first end 30 of the pad and to the bottom portion 13 of the electrode cup 12 whereby to bond the pad 23 to the bottom portion 13 of the electrically insulating cup structure 12.

The adhesive 26 may be located partially or completely at the lower surface of the pad end portion 30, that is, partially or completely within the confines of the pad 23. Alternatively, the adhesive 26 may be applied for attachment to a lateral pad portion which is practically included in the pad end portion 30.

The adhesive 26 may be applied to the cup bottom portion and/or to the pad 23 individually when the pad 23 is away from the bottom portion 13, or simultaneously when the pad 23 is in contact with the bottom portion 13.

Electrically insulating adhesives 26 are presently preferred for their minimum interference with the electrolytic process. The adhesive may be a synthetic resin adhesive, such as an epoxy or acrylic resin, or an elastomer, such as a styrene-butadiene elastomer, silicone or latex material. The adhesive may be applied by dauber or other applicators, nozzles, extruders and the like while in a liquid or low-viscosity state. The adhesive is preferably cured or otherwise transformed to a solid state before the electrolyte is applied to the pad 23.

A presently preferred family of adhesives comprises the so-called "hot melt adhesives." These are nonvolatile thermoplastic materials which are heated and applied in a molten state and which then solidify upon cooling to room temperature. A good exposition on hot-melt adhesives is contained in Chapter 8, by Thomas Flanagan, of the HANDBOOK OF ADHESIVE BONDING, edited by Charles V. Cadle [McGraw-Hill, 1973], and in the chapter on Pressure-Sensitive Adhesives, by Mitsuo Toyama and Toshio Ito, in POLYMER-PLASTICS TECHNOLOGY AND ENGINEERING, Vol. 2, edited by Louis Naturman [Mercer Dekker, Inc., New York, 1974] which also lists other suitable adhesives. Relevant patents which are herewith incorporated by reference herein include U.S. Pat. No. 2,999,769, entitled Pressure-Sensitive Adhesive Tape Employing Adhesive Containing Curable Polymer, a Liquid Lackifier and Aldehyde Resin Curing Agent, by Ralf Korpman, issued Sept. 12, 1961; and U.S. Pat. No. 3,342,902, entitled Hot Melt Adhesive Having Pressure Sensitivity Comprising Atactic Polypropylene, Ethylene-Vinyl Acetate Copolymer, and a Polyterpene.

Suitable adhesives of this general class include hot-melt compositions based on mixtures or resin tackifier and the block copolymer composed of styrene and butadiene or a copolymer of ethylene with vinyl acetate.

The electrode 18 in this preferred embodiment may include particles of electrode material, such as silver and silver chloride particles in an organic matrix for these particles.

In accordance with a preferred embodiment of the invention, the silver component of the electrode is interspersed in particulate form in the organic matrix of the electrode 18 with the silver chloride component which is also in particulate form.

Through various calculations and tests, I have determined preferred broad ranges of weight percentages relative to the weight of the organic matrix 14 and the silver particles 12 and silver chloride particles 13 interspersed in the organic matrix. According to these preferred ranges, the silver particles constitute substantially from 70 to 90% by weight, the silver chloride particles constitute substantially from 0.5 to 15% by weight, and the organic matrix constitutes essentially the balance of the weight of the organic matrix with the silver particles and silver chloride particles dispersed therein.

Generally, if the silver particles are shaped anisotropic (e.g. needle-shaped silver particles of silver flakes), the content of the silver particles can be lowered relative to the preferred higher content for spherical silver particles.

Preferably, the silver particles and the silver chloride particles are of a purity of about 99.9% or higher to avoid generation of spurious potentials from electrode contaminants. Spherical, needle-shaped and flaked silver particles of the desired purity are readily available commercially. Silver chloride particles of the desired purity are also commercially available from such suppliers as J. T. Baker Chemical Company, Phillipsburg, N.J., and Mallinckrodt Chemical Works, St. Louis, Mo.

Typically, the silver chloride particles are precipitated from an aqueous solution of a soluble silver salt and filtered and washed for providing the desired purity.

According to the subject invention, the matrix is of an electrically insulating material to avoid the occurrence of current-conducting paths within the matrix in parallel to the silver and silver chloride particles. The insulating material of the organic matrix is also water impermeable to prevent electrolyte contacting the electrode from providing ionic conduction within the matrix in parallel to the silver and silver chloride particles. The organic matrix is also of a material which is chemically inert to the electrolyte encountered by the electrode.

A large number of organic materials qualify for the electrode matrix, since there are many organic materials which are electrically insulating, water impermeable and chemically inert to the types of electrolyte encountered by silver, silver chloride electrodes. Those skilled in the art of organic chemistry or in the technology of electrical insulating materials will readily be able to identify a large number of suitable organic materials.

By way of example and not by way of limitation, it is well known that most resins are electrically insulating, water impermeable and chemically inert to the types of electrolyte (e.g. aqueous sodium chloride solutions in the case of bioelectrodes) encountered by silver, silver chloride electrodes.

By way of further examples, it is well known that most thermoplastic resins, thermosetting resins and elastomers or rubbers are electrically insulating, water impermeable and chemically inert in the above mentioned sense. These properties are also possessed by many high molecular weight waxes.

Typically, the silver particles consist essentially of solid or pure silver as mentioned above. However, the silver particles may alternatively be made of, or comprise, silver-coated particles of a material other than silver. In the context of the subject electrodes which function on the basis of surface phenomena, the expression silver particles as herein employed is intended to be broad enough to cover powders of silver, including particles of solid silver, and silver-coated particles of an inert material other than silver.

Suitable low-cost, low density substitutes for powders of solid silver particles include a product sold by Sigmatronics, of Moorestown, New Jersey, under the designation "Siliclad G-100 and consisting of a powder of finely divided ceramic particles essentially each of which has a uniform coating of essentially pure silver. Other substitutes include hollow silica microspheres designated Eccospheres SI (thin-walled bubbles made from silica) and hollow glass microspheres designated Eccospheres/Glass Microballoons, sold by Emerson & Cuming, Inc., of Canton, Mass., and provided with essentially pure silver coatings.

The silver coating may be applied to solid core particles or to hollow core particles by such well-known techniques as vacuum deposition, sputtering, precipitation of electroless plating, for instance. Inorganic materials other than ceramics and glass, or organic materials such as plastics resins, may be employed for the core particles on which the silver coating is deposited or plated, since silver coatings have in the past been successfully provided on a large variety of materials.

The above mentioned proportions, expressed in percent by weight, are subject to wide variation if silver substitute powders of silver layers coated on core particles having a density less than the density of silver are employed in lieu of or in combination with solid silver particles. For instance, the manufacturers of the above mentioned silvercoated ceramic particles indicate for their product a density of about one-third the density of silver. The manufacturers of the above mentioned hollow silica microspheres indicate for these microspheres a particle density of 0.26 g/cc and a bulk density of 0.18g/cc.

This makes it impractical to provide constituent ranges in percent by weight which would be generally applicable to solid silver particles and to silver-clad silver particles. Since the function of the silver and silver chloride constituents of the electrode proceeds chiefly on the basis of surface phenomena, it is appropriate under the circumstances to provide generally applicable ranges for silver particles, silver-clad silver particles, and silver chloride particles in terms of percent by volume.

I have in this respect determined through calculation and experiment preferred broad ranges of volume percentages relative to the volume of the organic matrix and the silver particles and silver chloride particles interspersed in the organic matrix of the electrode 18. According to these preferred ranges, the silver particles constitute substantially from 15 to 70% by volume, the silver chloride particles constitute substantially from 0.2 to 15% by volume, and the organic matrix constitutes essentially the balance of the volume of the organic matrix with the silver particles and silver chloride particles dispersed therein.

In similarity to the silver particles, the silver chloride particles could either be made of pure silver chloride or of silver chloride coated on an inert particle core.

Suitable working examples of epoxy resin matrix electrodes and styrene-butadiene elastomer matrix electrodes are contained in my above mentioned issued patent which is herewith incorporated by reference herein.

It will now be recognized that the subject invention considerably advances the bioelectrode art by radically departing from the state of the art course of development and by combining various features to best advantage in several novel combinations. With respect to the aspect of the disclosed invention concerning the anchoring of the electrolyte pad 23 by the adhesive 26, it will be recognized that this anchoring not only prevents the electrode from falling out of the cup, but also renders possible the illustrated and other highly advantageous electrode designs. The adhesive 26 may be inert, thereby avoiding any detrimental interference with the operation of the electrode. In this connection, it may be noted that the disclosed electrode pad anchoring technique may, within the scope of the corresponding claims, be applied to electrode structures other than those specifically shown in the drawings.

Various modifications and variations within the spirit and scope of the subject invention will be suggested or rendered obvious to those skilled in the art by the subject extensive disclosure.

I claim:
1. A bioelectrode applicable to a body part, comprising in combination:
   an electrically insulating structure having a bottom portion and a lateral wall portion defining a cavity;
   electric current conducting means including and electrode at said bottom portion;
   means for retaining electrolyte, including a pad of electrolyte-absorbent resilient material in said cavity contacting said electrode at said bottom portion and projecting out of said cavity in an electrolyte containing relaxed condition;
   a lateral space between said pad and said wall portion;
   a removable cover on said structure compressing said resilient pad completely into said cavity, said lateral space being of a size to completely accommodate said pad when compressed completely into said cavity by said cover; and
   means for attaching said structure to a body part.
2. A bioelectrode as claimed in claim 1, wherein: said wall portion is rigid.
3. A bioelectrode as claimed in claim 1, wherein: said wall portion is hollow-cylindrical; and said pad is laterally spaced from any part of said hollow-cylindrical wall portion.
4. A bioelectrode as claimed in claim 3, wherein: said wall portion is rigid.
5. A bioelectrode as claimed in claim 3, wherein: said pad is cylindrical; and said lateral space between said pad and said wall portion is annular.
6. A bioelectrode as claimed in claim 5, wherein: said wall portion is rigid.
7. A bioelectrode as claimed in claim 1, wherein: said pad has a top surface at said removable cover; and said removable cover has a lid portion which contacts all of said top surface.
8. A bioelectrode as claimed in claim 7, wherein: said lid portion is flat.
9. A bioelectrode as claimed in claim 1, wherein: said wall portion has a rim opposite said bottom portion; and said removable cover has an essentially flat lid portion contacting said rim and said pad.
10. A bioelectrode as claimed in claim 9, wherein: said wall portion is rigid.
11. A bioelectrode as claimed in claim 1, wherein: said pad is of hydrophilic material.
12. A bioelectrode as claimed in claim 1, including: means for anchoring said pad in said cavity.
13. A bioelectrode as claimed in claim 12, wherein: said anchoring means are located at said bottom portion.
14. A bioelectrode as claimed in claim 12, wherein: said anchoring means are included in said electrode at said bottom portion.
15. A bioelectrode as claimed in claim 12, wherein: said electrode at said bottom portion has an organic matrix; and said pad is anchored at said bottom portion with said organic matrix.
16. A bioelectrode as claimed in claim 12, wherein: said wall portion is rigid.
17. A bioelectrode as claimed in claim 12, wherein: said wall portion is hollow-cylindrical; and said pad is laterally spaced from any part of said hollow-cylindrical wall portion.
18. A bioelectrode as claimed in claim 17, wherein: said wall portion is rigid.
19. A bioelectrode as claimed in claim 17, wherein: said pad is cylindrical; and said lateral space between said pad and said wall portion is annular.
20. A bioelectrode as claimed in claim 19, wherein: said wall portion is rigid.
21. A bioelectrode as claimed in claim 12, wherein: said pad has a top surface at said removable cover; and said removable cover has a lid portion which contacts all of said top surface.
22. A bioelectrode as claimed in claim 21, wherein: said lid portion is flat.
23. A bioelectrode as claimed in claim 12, wherein: said wall portion has a rim opposite said bottom portion; and said removable cover has an essentially flat lid portion contacting said rim and said pad.
24. A bioelectrode as claimed in claim 23, wherein: said wall portion is rigid.
25. A bioelectrode as claimed in claim 12, wherein: said pad is of hydrophilic material.
26. A bioelectrode as claimed in claim 1, including:

a central aperture in said pad where said pad projects out of said cavity for receiving an electrolyte.

27. A bioelectrode as claimed in claim 12, wherein: said anchoring means include an adhesive anchoring said pad to said bottom portion of said electrically insulating structure.

28. A bioelectrode comprising in combination:
a silver, silver chloride electrode comprising a plurality of silver particles, a plurality of silver chloride particles, and an electrically insulating, water impermeable, inert organic matrix for said silver particles and said silver chloride particles, said silver particles and said silver chloride particles being interspersed with each other in and throughout said matrix, and said interspersed silver particles and silver chloride particles being in electrical contact with each other;
an electrical conductor connected to said silver, silver chloride electrode;
means for retaining an electrolyte at said silver, silver chloride electrode;
container means for said silver, silver chloride electrode and for at least part of said conductor and said electrolyte-retaining means;
an adhesive between said electrolyte retaining means and said container means, said adhesive being independent of said matrix and anchoring said electrolyte retaining means in said container means;
said silver particles being present in said organic matrix in an amount of from 15 to 70% by volume of said organic matrix with said interspersed silver particles and silver chloride particles;
said silver chloride particles being present in said organic matrix in an amount of from 0.2% to 15% by volume of said organic matrix with said interspersed silver particles and silver chloride particles; and
said organic matrix constituting essentially the balance of the volume of said organic matrix with said interspersed silver particles and silver chloride particles.

29. A bioelectrode as claimed in claim 28, wherein: said electrolyte-retaining means include a sponge anchored by said adhesive in said container means.

30. A bioelectrode as claimed in claim 28, wherein: said organic matrix is an epoxy resin matrix.

31. A bioelectrode as claimed in claim 28, wherein: said organic matrix is elastomeric.

32. A bioelectrode as claimed in claim 28, wherein: said adhesive is a synthetic resin adhesive.

33. A bioelectrode as claimed in claim 28, wherein: said adhesive is a hot-melt adhesive.

34. A bioelectrode as claimed in claim 28, wherein: said adhesive is elastomeric.

35. A bioelectrode comprising in combination:
a silver, silver chloride electrode comprising a plurality of silver particles, a plurality of silver chloride particles, and an electrically insulating, water impermeable, inert organic matrix for said silver particles and said silver chloride particles, said silver particles and said silver chloride particles being interspersed with each other in and throughout said matrix, and said interspersed silver particles and silver chloride particles being in electrical contact with each other;
an electrical conductor connected to said silver, silver chloride electrode;
means for retaining an electrolyte at said silver, silver chloride electrode;
container means for said silver, silver chloride electrode and for at least part of said conductor and said electrolyte-retaining means;
an adhesive between said electrolyte retaining means and said container means, said adhesive being independent of said matrix and anchoring said electrolyte retaining means in said container means;
said silver particles being present in said organic matrix in an amount of from 70 to 90% by weight of said organic matrix with said interspersed silver particles and silver chloride particles;
said silver chloride particles being present in said organic matrix in an amount of from 0.5 to 15% by weight of said organic matrix with said interspersed silver particles and silver chloride particles; and
said organic matrix constituting essentially the balance of the weight of said organic matrix with said interspersed silver particles and silver chloride particles.

36. A bioelectrode as claimed in claim 35, wherein: said electrolyte-retaining means include a sponge anchored by said adehsive to said container means.

37. A bioelectrode as claimed in claim 35, wherein: said organic matrix is an epoxy resin matrix.

38. A bioelectrode as claimed in claimed 35, wherein: said organic matrix is elastomeric.

39. A bioelectrode as claimed in claim 35, wherein: said adhesive is a synthetic resin adhesive.

40. A bioelectrode as claimed in claim 35, wherein: said adhesive is a hot-melt adhesive.

41. A bioelectrode as claimed in claim 35, wherein: said adhesive is elastomeric.

* * * * *